(12) United States Patent
Kent (10) Patent No.: US 10,810,906 B2
(45) Date of Patent: Oct. 20, 2020

(54) PROVIDING DERMATOLOGY-SPECIFIC TRAINING TO PRIMARY CARE PROVIDERS

(71) Applicant: Dermatology Professional Educators, LLC, Macon, GA (US)

(72) Inventor: David E. Kent, Macon, GA (US)

(73) Assignee: DERMATOLOGY PROFESSIONAL EDUCATORS, LLC, Macon, GA (US)

( * ) Notice: Subject to any disclaimer, the term of this patent is extended or adjusted under 35 U.S.C. 154(b) by 966 days.

(21) Appl. No.: 14/809,869

(22) Filed: Jul. 27, 2015

(65) Prior Publication Data

US 2016/0027339 A1   Jan. 28, 2016

Related U.S. Application Data

(60) Provisional application No. 62/029,131, filed on Jul. 25, 2014.

(51) Int. Cl.
| | |
|---|---|
| G09B 23/28 | (2006.01) |
| G06F 19/00 | (2018.01) |
| G16H 50/20 | (2018.01) |
| G09B 5/12 | (2006.01) |
| G09B 19/00 | (2006.01) |

(52) U.S. Cl.
CPC ........... G09B 23/28 (2013.01); G06F 19/321 (2013.01); G09B 5/12 (2013.01); G09B 19/00 (2013.01); G16H 50/20 (2018.01)

(58) Field of Classification Search
CPC ............... G06F 19/3418; G06F 19/325; G06F 19/3462; G06F 19/34; G16H 10/60; G16H 40/20; G16H 50/20; G16H 20/10; G16H 50/30; G16H 50/70; G16H 70/20; G16H 20/00; G16H 70/40; G06Q 50/24; G06Q 10/1095; A61B 5/444; A61B 5/445
USPC ........................................................ 705/2, 3
See application file for complete search history.

(56) References Cited

U.S. PATENT DOCUMENTS

| | | | | |
|---|---|---|---|---|
| 6,991,464 | B2* | 1/2006 | Liebert ................... | G06Q 50/24 434/236 |
| 7,894,651 | B2* | 2/2011 | Gutkowicz-Krusin ................ | A61B 5/0059 382/128 |
| 8,109,875 | B2* | 2/2012 | Gizewski ............. | A61B 5/0059 600/300 |
| 8,538,770 | B2* | 9/2013 | Papier ................... | G06F 19/324 705/2 |
| 8,635,084 | B2* | 1/2014 | Phillips ............... | G06F 19/3418 705/2 |
| 9,974,612 | B2* | 5/2018 | Pinter .................. | A61B 5/0008 |
| 2008/0020361 | A1* | 1/2008 | Kron ........................ | G09B 5/02 434/262 |

(Continued)

*Primary Examiner* — Victoria P Augustine
*Assistant Examiner* — Teresa S Williams
(74) *Attorney, Agent, or Firm* — Thomas Horstemeyer, LLP (57) ABSTRACT

Disclosed are various embodiments for providing dermatology-specific training to primary care providers. Primary care providers may register on the system and request access to various dermatology training materials. The primary care provider may be provided with the requested dermatology training materials when the primary care provider has a valid account. Payment may be required before a primary care provider can access the dermatology training materials.

20 Claims, 8 Drawing Sheets

(56) References Cited

U.S. PATENT DOCUMENTS

| | | | |
|---|---|---|---|
| 2008/0091471 A1* | 4/2008 | Michon | G06Q 40/08 705/3 |
| 2012/0315616 A1* | 12/2012 | Fourman | G09B 7/02 434/350 |
| 2013/0060576 A1* | 3/2013 | Hamm | G06F 19/3418 705/2 |
| 2013/0226601 A1* | 8/2013 | Razmi | G06F 19/3418 705/2 |
| 2015/0101066 A1* | 4/2015 | Fram | G06F 16/95 726/28 |
| 2015/0230712 A1* | 8/2015 | Aarabi | A61B 5/0077 600/476 |

* cited by examiner

PROVIDING DERMATOLOGY-SPECIFIC TRAINING TO PRIMARY CARE PROVIDERS

CROSS-REFERENCE TO RELATED APPLICATIONS

This application is a non-provisional application of, and claims priority to, co-pending U.S. Provisional Application entitled "PROVIDING DERMATOLOGY-SPECIFIC TRAINING TO PRIMARY CARE PROVIDERS," filed on Jul. 25, 2014, and assigned application No. 62/029,131, which is incorporated herein by reference in its entirety.

BACKGROUND

Dermatology is a specific field of practice for physicians relating to the treatment of skin conditions. Those physicians who practice dermatology are known as dermatologists. In addition to having a medical degree, dermatologists have dermatology-specific training consisting of an internship, a residency and continuing education. Such training may comprise four or more years of additional clinical training beyond medical school. Residency positions for dermatologists, in particular, may be extremely competitive, and Board certification examinations may be difficult. With only 325 new dermatologists completing training each year, the Dermatology Foundation predicts that by the year 2040, there will be only about 2.8 dermatologists providing care per 100,000 people in the United States. Accordingly, the demand for dermatology services may exceed the supply of dermatology providers. In some cases, specially trained physician assistants and nurse practitioners may associate with dermatologists to provide dermatology services. Such training may also amount to multiple years of education.

Primary care providers correspond to primary care physicians, physician assistants, nurse practitioners, and others who are engaged in the practice of providing primary care to patients. For example, primary care physicians may be trained in family practice or internal medicine. Primary care providers are the medical personnel with more of a long-standing relationship with patients. Patients may see primary care providers when they are ill or for regular checkups. Primary care providers are trained to diagnose and treat a variety of conditions, but they are generalists, not specialists. Due to requirements by health insurance plans, patients are often required to see a primary care provider to obtain a referral to a specialist so that that the visit to the specialist may be covered by insurance. Since a visit to a specialist is often more expensive than a visit to a primary care provider, the hope is that the primary care provider will be able to resolve the issue. Unfortunately, most primary care providers do not have sufficient training in dermatology, and thus may have to refer the patient. In some cases, lack of training may result in the primary care provider overlooking or disregarding skin conditions that may benefit from treatment.

BRIEF DESCRIPTION OF THE DRAWINGS

For a more complete understanding of the embodiments and the advantages thereof, reference is now made to the following description, in conjunction with the accompanying figures briefly described as follows.

The drawings illustrate only example embodiments and are therefore not to be considered limiting of the scope described herein, as other equally effective embodiments are within the scope and spirit of this disclosure. The elements and features shown in the drawings are not necessarily drawn to scale, emphasis instead being placed upon clearly illustrating the principles of the embodiments. Additionally, certain dimensions or positionings may be exaggerated to help visually convey certain principles. In the drawings, similar reference numerals between figures designate like or corresponding, but not necessarily the same, elements.

DETAILED DESCRIPTION

The present application relates to approaches for providing training in the field of dermatology to primary care providers, including real-time consults with dermatologists. Providing dermatological training to primary care providers has many advantages. With some specific education, many common skin conditions may be treated by primary care providers. 20-35 percent of all visits to primary care providers and urgent care centers involve at least one skin complaint, and in 58-72 percent of these cases it is their chief complaint. More often than not, primary care providers refer patients to dermatologists for conditions they could easily diagnose and successfully treat in-house. Accordingly, the need to refer patients to dermatologists may be reduced, thereby reducing time and costs involved in treating the conditions. A reduced patient load will help alleviate waiting times currently experienced by patients in visiting dermatology practitioners. In addition, dermatological training may help primary care practitioners identify dangerous skin conditions at the earliest stages and refer such patients immediately to specialists for further treatment, thereby improving patient outcomes.

It is important to recognize that conventional training for primary care providers has not resulted in adequate preparation. Standard dermatology training is lacking in primary care medicine. Most primary care providers simply do not feel confident with respect to dermatology. For example, primary care providers may have had as little as two to four weeks of training in medical school or residency on the subject of dermatology. Although they may have seen a variety of skin conditions, the default reaction of most primary care providers may be to refer the patients for further diagnosis and treatment.

The innovative approaches described herein recognize that primary care providers do not have enough time to sit through conventional classes and training. Providing dermatological training in a convenient, concise, and digestible format will lead to wide adoption by primary care providers. For example, online delivery may be employed to facilitate convenient self-study.

In various embodiments, the educational training may be divided into multiple modules. Each module may cover a specific class or category of conditions in a self-contained way. By dividing the training into multiple modules, primary care providers may pick and choose areas that are most important to their practice. For example, if a primary care provider is especially interested in diagnosing and treating acne, the primary care provider may utilize a training module specific to acne, perhaps without utilizing other modules. Since primary care providers may have a shortage of available time, this will enable primary care providers to have dermatological training in the areas that are most relevant to them, with any additional training resulting in a benefit to their patients over no training. Non-limiting examples of simple office procedures that can be performed by primary care providers include skin biopsy, management of benign and premalignant skin lesions, and treating non-facial skin cancers.

Dermatology training within a primary care practice will not only help retain existing patients, but will also help attract new patients with skin care needs. As compared with other medical fields, dermatology is especially susceptible for training of and treatment by primary care providers. Skin conditions are often identified by sight. Consequently, images and videos of examples of skin conditions are particularly helpful. Further, images and videos may be easily delivered via an online format. Additionally, utilizing audio in the video teaching of dermatology helps focus attention to important details that might otherwise be missed.

In preparing dermatological training materials, it is helpful to have the direction of an experienced dermatology provider. An experienced dermatology provider, such as a dermatologist with years of experience, may have resources such as photos and videos of patients with a variety of skin conditions. Since skin conditions may present differently based upon the person, having an extensive library is important.

Components of a dermatological training program may include, for example: developing the physical exam skills necessary to differentiate between diseases that look alike; successful management protocols, including how to approach non-responders, what to change and why; using clinical scenarios routinely seen in dermatology practices to illustrate key teaching points; quality videos illustrating specific step-by-step details of common office procedures; and managing patient expectations and improving outcomes.

The training programs discussed herein bring new horizons to primary care by taking a different approach to dermatology training. Conventional training programs on the market are diagnosis-driven, with little follow-up instruction on how to provide continued care of a patient or how to manage an ongoing condition. Instead, the training program discussed herein takes a broader approach to treating patients with dermatology needs on an ongoing basis.

The training program discussed herein may stress practical dermatologic problem solving and disease management, providing an educational experience that focuses on total patient care—from diagnosis of common skin conditions and lesions, to developing a treatment plan and establishing skin care management. Accordingly, it allows primary care physicians, nurse practitioners, and physician assistants to learn the knowledge and skill set necessary to evaluate, diagnose, treat and manage common skin conditions. Each training module may blend a variety of educational multimedia audio, images or videos of real dermatology patients, and step-by-step procedural videos to focus and increase learning as well as provide a complete training experience.

The program described herein is designed for primary care providers based at least in part on visual learning methodology. It focuses on the fundamentals of the dermatologic exam, emphasizing recognition of key exam findings and pattern recognition so that medical providers will know what to look for so they will know what they are looking at. Because dermatology is driven by visual diagnosis, the program described herein uses real-patient photography to illustrate skin conditions discussed in each module—from common acne and eczema to melanoma and other skin cancers. Pulling from real-patient examples, the clinical scenarios in each module demonstrate common patterns of patient presentation, as well as how to approach patients who do not improve and what adjustments to make when conditions change.

The program described herein makes learning and information retention easy so the primary care provider can quickly grasp key dermatology facts, concepts, and procedures to effectively treat patients with skin conditions. The program may be divided into module topics, such as "Acne" and "Eczema." Providers may sign up for the whole program, start with select individual modules, or bundle starter modules with a professional-level package.

Each trainee is able to move through the selected module at his or her own pace, providing adequate time to absorb new learning topics fully. By the end of the training program, primary care providers will be able to accurately and correctly identify physical exam findings, diagnose, treat, and develop a management plan for the ongoing care of the patient. In one embodiment, users are also granted login access to an extensive image library with quick-reference diagnosis, treatment, and management information based at least in part on the training.

Non-limiting examples of modules will next be discussed. In a common office procedures module, primary care providers learn to perform the top dermatologic office procedures to diagnose and treat numerous skin conditions, featuring detailed instructional videos with audio emphasizing key points of each procedure and improving patient outcomes. Key concepts may include: diagnostic and therapeutic procedures with step-by-step, easy to follow videos; deciding which procedure to offer or perform; therapeutic goals, indications, contraindications, potential risks and management of unintended consequences; achieving successful results and avoiding poor results or adverse events; and insuring patient safety.

In an acne module, primary care providers learn how to diagnose, classify, treat and manage acne, the number one reason patients see a dermatologist, characterized by primary lesions (e.g., papules, pustules, cysts) and inflammation. Key topics may include the following: understanding and making the diagnosis of acne; classifying and grading acne; appropriate and successful treatments according to acne grade; no improvement in the acne of the patient: now what?; additional causes of acne; and clinical case studies and procedural videos to guide you.

In an eczema module, primary care providers learn how to diagnose, classify, treat and manage eczema (dermatitis), characterized as an inflammatory condition with itchy rashes that look alike. Key topics may include: what is eczema?; physical exam and timeline of presentation; meaningful classification of eczemas and keys to successful management; identification reactions: removing the mystery; and clinical scenarios.

In an atopic dermatitis module, primary care providers learn how to diagnose, treat and manage atopic dermatitis, characterized as a chronic, pruritic rash. Key topics may include: pathogenesis of atopic dermatitis and triggers of disease; clinical presentations classified by age group; therapeutic principles and management; infectious complications; and clinical scenarios.

In a seborrheic dermatitis module, primary care providers learn how to diagnose, treat, and manage seborrheic dermatitis, a common inflammatory skin disorder in the papulosquamous category. Key topics may include the following: characteristics and physical exam, therapy and management, differentiation from other rashes, and clinical scenarios.

In a benign lesions module, primary care providers learn how to identify benign lesions, the most common skin finding in patients seeking treatment for epidermal tumors, as well as how to treat, manage, and monitor patients with benign lesions. In a premalignant lesions module, primary care providers learn how to identify and treat premalignant skin lesions and common precancerous epidermal growths. In a malignant lesions module, primary care providers learn how to identify malignant (cancerous) lesions, such as basal cell carcinoma, squamous cell carcinoma, malignant melanoma and other skin cancers, as well as how to treat and manage patients with selected malignant lesions.

In a physical exam module, primary care providers learn how to identify and manage common skin problems that regularly present in a primary care practice. Key concepts may include the following: mastering the dermatologic diagnosis, making a diagnosis based at least in part on a few key physical findings, and identifying the underlying cause of a skin condition.

In a module on maintaining healthy skin, primary care providers learn how to maintain healthy skin in your patients by using over the counter products. Key concepts may include the following: skin structure; the importance of skin barrier functions; percutaneous absorption of topical medications; body surface area and absorption differences; medication required to cover body areas; how to apply moisturizers, topical steroids, antipruritics, and others; sunscreens and sunblock; topical preparations; understanding pregnancy and lactation skin problems; and brand vs. generic product definitions, costs, and discounts.

In a rosacea module, primary care providers learn how to diagnose, treat and manage rosacea, a skin condition characterized by red splotches that appear on the face of the patient. In a bites, stings, and infestations module, primary care providers learn how to diagnose, treat, and manage animal and insect bites, stings, and infestations. In an obesity dermatitis module, primary care providers learn how to diagnose, treat, and manage skin conditions and problems associated with obesity.

In a hives module, primary care providers learn how to diagnose, treat, and manage hives and allergic reactions, plus practical guidelines for management. In a hair and nail problems module, primary care providers learn simplified classification, diagnostic clues and the management of common causes of hair loss. Primary care providers also learn to identify common nail disorders, practical management, and indications for referral. In a holiday dermatitis module, primary care providers learn how to identify and treat skin problems that arise during the holiday seasons, including, but not limited to the following: sunburns, jellyfish stings, heat rash, frost bite, and wind burn.

In an immune dysfunction module, primary care providers learn how to identify, and manage skin problems seen with increased frequency in patients with an altered immune system, including, but not limited to cancer patients and patients with HIV. In a psoriasis module, primary care providers learn key concepts about psoriasis, including, but not limited to, disease classification and fundamental management principles. In a common skin infections and problems module, primary care providers learn key points about common skin infections, including diagnosing and treating bacterial infections, viral infections and fungal infections, as well as pink eye and other common skin problems. In a pityriasis rosea module, primary care providers learn key facts, clinical presentations, and diagnosis/management suggestions.

In a therapeutics and prescription quick reference module, primary care providers may access a quick cross-reference of diseases and recommended therapeutics, along with a listing of the corresponding modules where additional information on the disease may be found.

Access to the modules of the dermatological training program may be by way of a paid subscription. For example, a user may subscribe to one or more modules for access for a specified term, such as one year. Multiple modules may be bundled together at enhanced subscription levels. Renewals may be facilitated by payment of a lower renewal price. Renewals may be beneficial for access to additional and updated materials. Renewals may provide access to videos on additional office procedures including aesthetics and cosmetic procedures, as well as a periodic newsletter, with seasonal skin tips, product highlights and other valuable dermatology-focused information.

Figure 1:
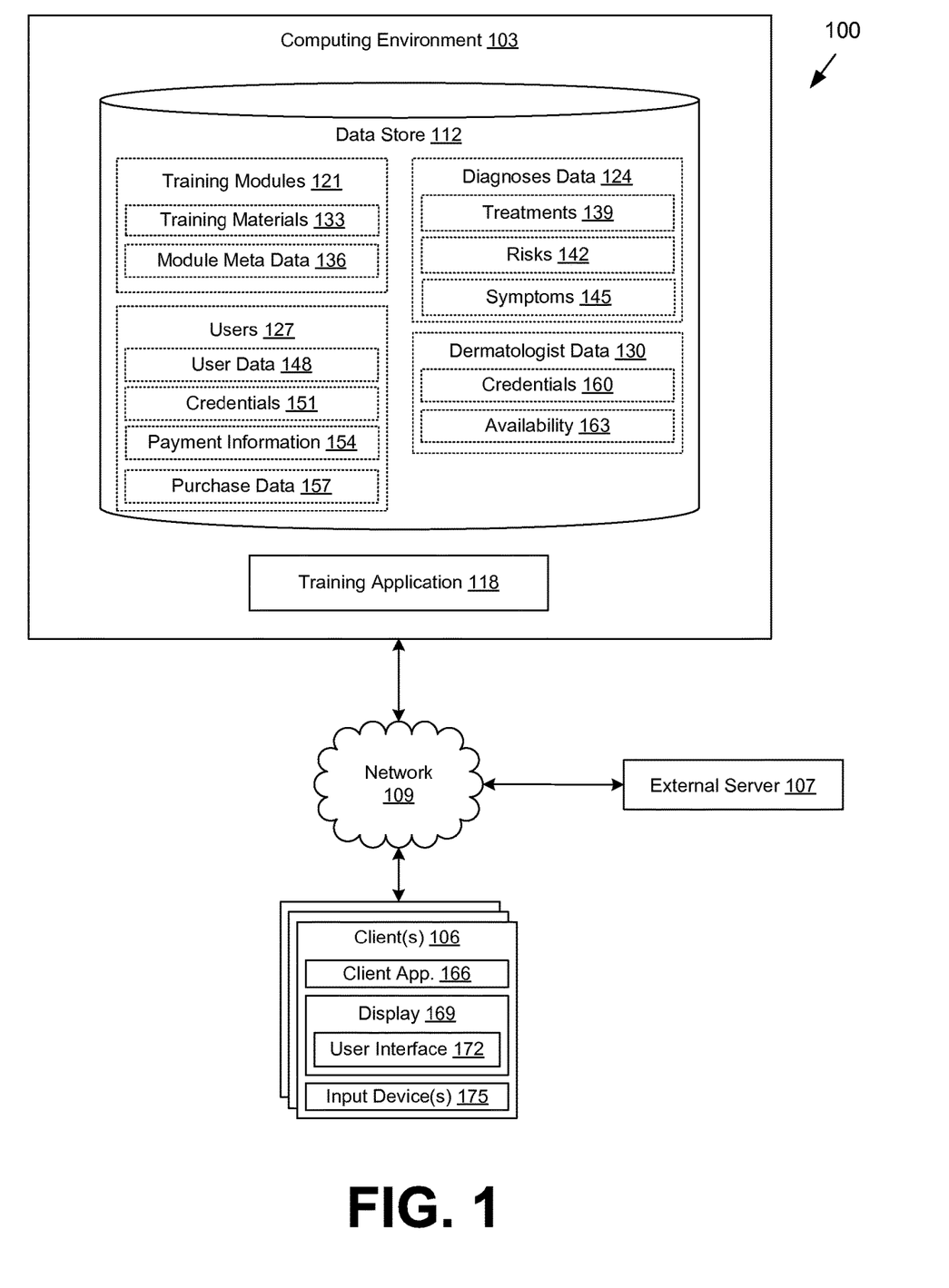
FIG. 1 illustrates a networked environment according to various example embodiments.

With reference to FIG. 1, shown is a networked environment 100 according to various embodiments. The networked environment 100 includes a computing environment 103, one or more clients 106, and external server 107 in data communication via a network 109. The network 109 includes, for example, the Internet, intranets, extranets, wide area networks (WANs), local area networks (LANs), wired networks, wireless networks, cable networks, satellite networks, or other suitable networks, etc., or any combination of two or more such networks. In some scenarios, the one or more clients 106 may include personal mobile clients. The external server 107 may be any computing device, computing environment, data provider, service provider, or computing resource provider, which may be provided by a third-party or by the provider of computing environment 103.

The computing environment 103 may comprise, for example, a server computer or any other system providing computing capability. Alternatively, the computing environment 103 may employ a plurality of computing devices that may be arranged, for example, in one or more server banks or computer banks or other arrangements. Such computing devices may be located in a single installation or may be distributed among many different geographical locations. For example, the computing environment 103 may include a plurality of computing devices that together may comprise a hosted computing resource, a grid computing resource, and/or any other distributed computing arrangement. In some cases, the computing environment 103 may correspond to an elastic computing resource where the allotted capacity of processing, network, storage, or other computing-related resources may vary over time.

Various applications and/or other functionality may be executed in the computing environment 103 according to various embodiments. Also, various data may be stored in a data store 112 that is accessible to the computing environment 103. The data store 112 may be representative of a plurality of data stores 112 as can be appreciated. The data stored in the data store 112, for example, is associated with the operation of the various applications and/or functional entities described below. The components executed on the computing environment 103, for example, include a training application 118, and other applications, services, processes, systems, engines, or functionality not discussed in detail herein.

The training application 118 may be executed to provide dermatology training materials to doctors, such as primary care physicians. Dermatology training materials may be implemented in the computing environment 103 and accessed via a training application 118. The training application 118 may restrict access to the dermatology training materials if a user does not currently have an active subscription. The training application 118 may also search the data store 112 or other sources for training materials, such as training modules using criteria specified by a user of the system. The training application 118 may receive criteria describing a dermatology condition, such as one or more affected areas and one or more symptoms including visual characteristics, temporal characteristics, locational characteristics, experience based characteristics, and other aspects of the dermatology condition.

The training application 118 may generate a user interface comprising results from the search and cause the user interface to be rendered by one or more clients 106. For example, the training application 118 may cause client 106 to render the user interface by transmitting a web page to a web browser executed on client 106 or by transmitting information describing the search results to the client application, where the client application may be programmed to render a user interface including the search results. The training application 118 may obtain an image or video illustrating a symptom on a patient from a client 106. For example, the client application may capture an image, video, or other data from one or more input devices and transmit that data to training application 118.

The training application 118 may process the image, video, or other data, such as using pattern recognition, and determine one or more characteristics of one or more symptoms. For example, a temperature reading of a patient may indicate that a patient has a fever, or a weight of the patient may be compared by the training application 118 to medical records of the patient to determine that a recent change in weight has occurred. As another example, picture of a marking on skin may be processed to determine the size of the marking, color of the marking, and location of the marking on the body. A subsequent picture of the marking at a later time may be compared to an earlier image, such as one stored in user data 148, to determine that the marking as increased or decreased in size, changed color, darkened, lightened, changed from a consistent color to a varied color, or other changes that may be recognized. The training application 118 may also determine that a subsequent picture illustrates an area of the body has increased in size from an earlier picture, for example, from a swelling of the body part or area of the body.

The training application 118 may generate one or more potential diagnoses from using determined or obtained criteria. For example, the training application 118 may compare the criteria to the symptoms 145 in diagnoses data 124 to determine one or more potential diagnoses. The training application 118 may calculate risks of a negative impact to the patient from treating the determined one or more diagnoses. The training application 118 may calculate a risk of treating each of the potential diagnoses, such as by using risk 142 or an external source of data, such as external server 107. For example, the training application 118 may determine that the medicine associated with one of the potential diagnoses, such as chemotherapy for cancer, may negatively impact to the patient, such as causing a drug having negative side effects, and alert a user of the risks associated with the potential diagnosis. The negative impact to a patient may include a risk associated with mixing current medications of the patient, a risk of side effects from medicine used to treat a condition, and other types of risks described herein.

The training application 118 may determine a likelihood that a treatment for one of the potential diagnoses negatively impact a patient having a different one of the potential diagnoses. In this situation, the user may want to take extra precautions prior to prescribing a treatment in case the diagnosis is incorrect and the treatment could negatively affect the patient. The training application 118 may determine that either the likelihood or the calculated risk exceeds a predefined threshold prior to recommending or initiating precautionary measures. The training application 118 may take a precaution of recommending a consult with a dermatologist prior to treating the patient based at least in part on the risks associated with the potential diagnosis, for example, to prevent undergoing unnecessary risky treatments if a patient may have different disease.

The training application 118 may be executed to provide and stream video and audio to users in a video conference using one or more clients 106. The training application 118 may be a single executable or may be multiple executables. The training application 118 may obtain a request from a user to consult with another doctor, such as a dermatologist. The request may include one or more criteria for one or more doctors for the consult. For example, a primary care physician may request a consult with three doctors, each being a board certified dermatologist specialized in skin cancer, having at least experience of five years, and accepting "GreenPlus GreenSword" insurance company. The training application 118 may search dermatologist data 130 and/or users 127 for individuals presently available for a consult with the user.

The training application 118 may initiate a video conference with the user and each of the one or more doctors that meet the criteria specified by the doctor. A client 106 associated with each of the one or more doctors may display a notification that the user wishes to consult with an option to accept or deny. The client 106 may display details of the case including payment estimates based at least in part on the patients insurance company and the severity of the case. The training application 118 may determine a start, an end time, and a total time of the consult. The training application 118 may calculate a cost to charge the user using the information related to the consult, such as the total time. The training application 118 may submit a claim to an insurance company associated with a patient of the user for the cost of the consult.

The training application 118 may obtain medical records and/or identifying information from a user for one or more patients. The training application 118 may query external server 107 to obtain medical records for a patient based at least in part on identifying information from a user. The identifying information may include consent for the computing environment 103 to access medical records for the patient. The training application 118 may support displaying an overlay of a user interface for a consult. The user interface may include an option to display the medical records for a patient to one or more doctors in the consult and/or to the user. The training application 118 may connect to a third-party system to obtain medical records using the consent and/or the identifying information.

The consent may be transmitted as a security key, such as a digital or electronic security key. For example, a patient or primary care physician may be assigned the security key that is required to access medical records of a patient from a third-party medical records provider. In some embodiments, a primary care physician may have a single security key for access to medical records for a patient of the primary care physician and the primary care physician may add patients to his or her security key (or an account associated with the security key) to obtain access to medical records of that patient. The consent given to the training application 118 may also be limited by time or extent of access. For example, a physician may have a security key for access to a medical record of the patient, but may generate a new key authorized for the training application 118 that is only authorized to access the account for a limited time and/or for a limited subset of the medical records of the patient.

The data stored in the data store 112 includes, for example, training modules 121, diagnoses data 124, users 127, dermatologist data 130, and potentially other data. The training module 121 may include various training materials 133 and module metadata 136. The diagnoses data 124 may include treatments 139 for various diagnoses, risks 142 that may be associated with the diagnoses or the treatment of the diagnoses, and symptoms 145 for the diagnoses. Users 127 may include user data 148, credentials 151, payment information 154, and purchase data 157. Users 127 may include primary care physicians and dermatologists, among other doctors and supporting staff, such as nurses and physicians assistants. The user data 148 may include profile information, such as name, address, and contact information. The user data 148 may also include patient records for one or more patients associated with one or more users. The patient records may be imported from external server 107 in compliance with Health Insurance Portability and Accountability Act (HIPAA) laws.

The credentials 151 may include various credentials for a user such as college degrees, certificates, board certifications, expertise, training, awards, recognition, years of experience, completed training modules 121, feedback from other users including feedback for attitude, bedside manner, and various competences. The dermatologist data 130 may include data linked to one or more user 127 or may be separate from user 127. The dermatologist data 130 may include credentials 160 and availability 163 of the dermatologist. The credentials 160 may be the same as credentials 151 and may also include skills in various specific practice areas in dermatology. The availability may include times during the week that a dermatologist is available for a video conference. The availability may also be a flag indicating that a dermatologist is currently logged into system awaiting a video conference.

The one or more clients 106 may include a client application 166, display 169 with a user interface 172, and input devices 175. The input devices 175 may include a touch screen, a microphone, a camera, one or more orientation sensors, a pressure sensor, a temperature sensor, an external medical device such as a blood pressure monitor or a scale. The input devices 175 may also include a specialized camera, such as a camera configured to insert into an ear of a user or a camera configured to take pictures of skin under a microscope.

The client application 166 of the client 106 may render the content on the display 169. The client application 166 may also render various user interfaces on the display 169 using the extrinsic data to enhance the user experience. The user interfaces may be dynamically updated as a consultation progresses in the foreground or in the background. Non-limiting examples of such user interfaces are shown and will be described in connection with FIGS. 2-6.

Figure 2:
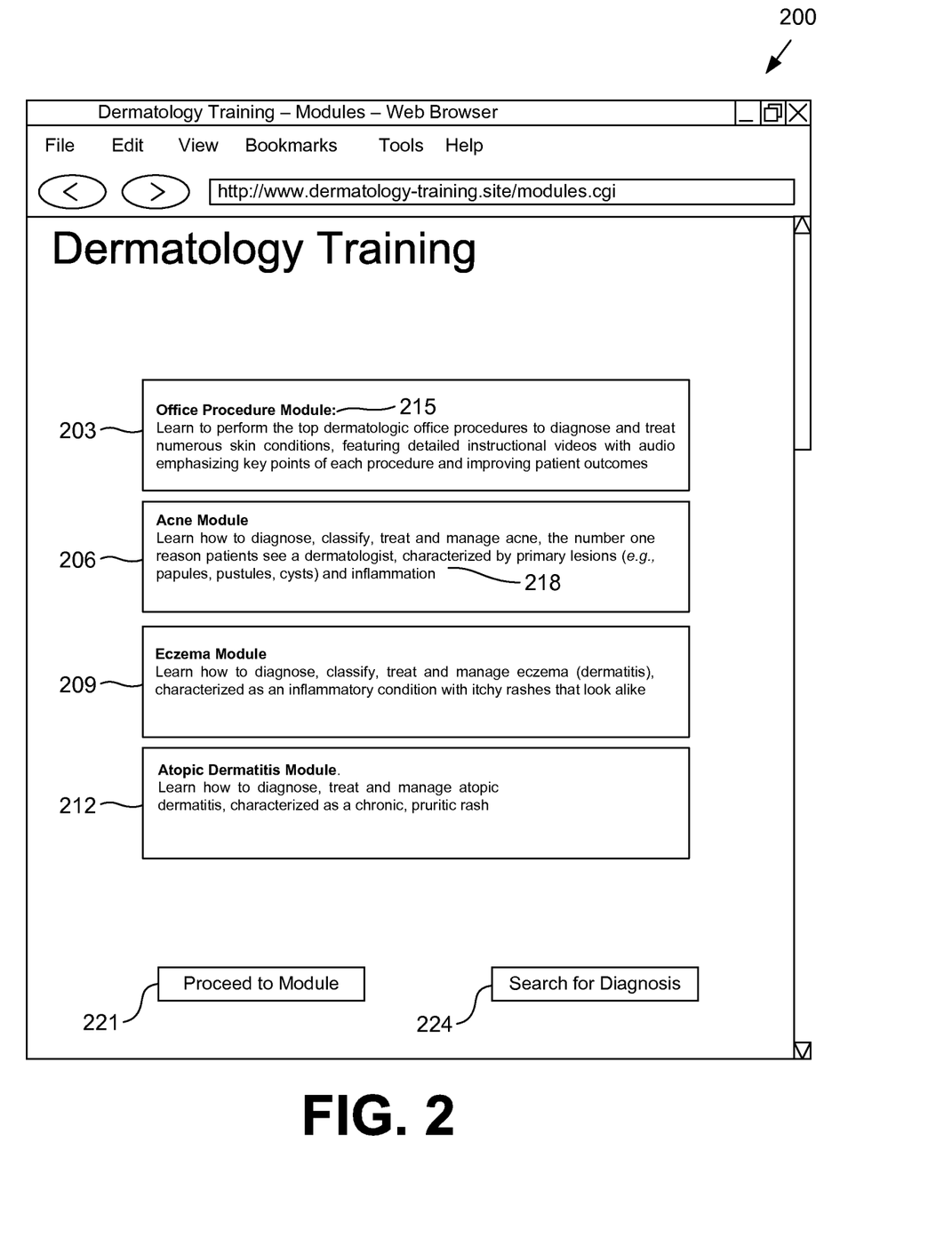
FIG. 2 illustrates a user interface rendered by a client in the networked environment of FIG. 1 according to various example embodiments.

With reference to FIG. 2, shown is an illustration of a module user interface 200 rendered on a display 169 (FIG. 1) of a client 106 (FIG. 1) in the networked environment of FIG. 1. The module user interface 200 may include one or more modules, such as office procedure module 203, acne module 206, eczema module 209, atopic dermatitis module 212, and various other modules. Each module may include a title 215 and a description 218. In some embodiments, a user may select a module by clicking the module, such as clicking within the box of office procedure module 203. In other embodiments, clicking the module highlights the module, such as by greying the box of the item, and a user must select a user interface element, such as Proceed to Module button 221. The module user interface 200 may also include a search button, such as search for diagnosis button 224.

The module may include a check box to indicate which one or more of the module is currently selected. A user may also add selected modules to a cart to purchase access and/or bookmark the modules to view later. The module user interface 200 may also include a user interface element to initiate a search for a diagnosis, according to embodiments described herein. When a module is proceeded to, a user may advance to begin training in the content of the module. For example, a user that selects the office procedure module may proceed to train using an embodiment according to FIG. 3.

Figure 3:
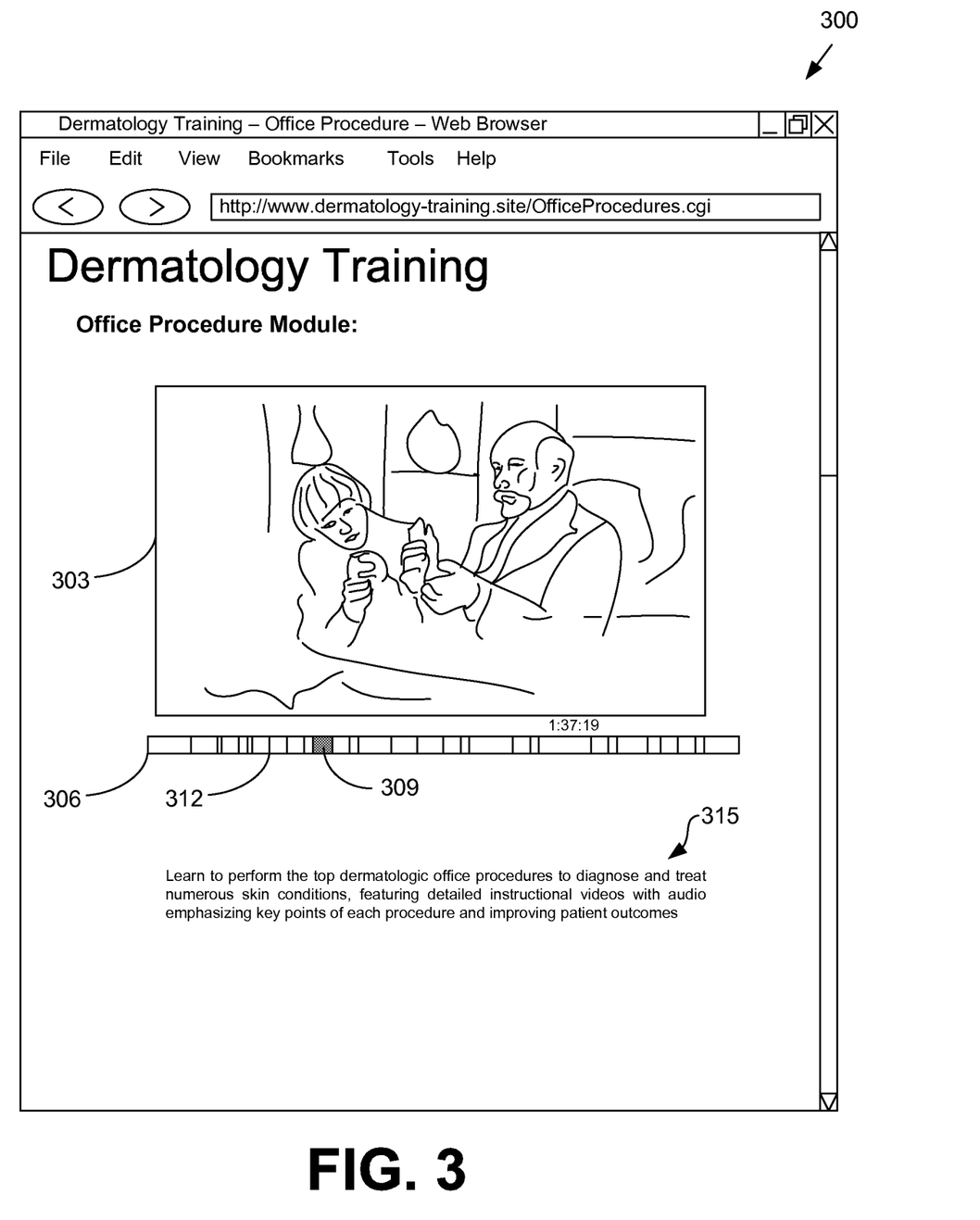
FIG. 3 illustrates a user interface rendered by a client in the networked environment of FIG. 1 according to various example embodiments.

With reference to FIG. 3, shown is an illustration of a training user interface 300 rendered on a display 169 (FIG. 1) of a client 106 (FIG. 1) in the networked environment of FIG. 1. The training user interface 300 may include one or more videos and/or audio recordings 303, a timeline 306 with a current position 309 and one or more bookmarks 312, and a written description 315. The training user interface 300 may provide various instructions to teach a user the subject matter for one or more of the training modules 121 (FIG. 1) selected by a user. For example, the training user interface 300 may show a video with audio of a doctor discussing office procedures and showing examples of proper office procedures. In this example, the training user interface 300 may also show a written description 315 describing the steps in real time that the video is discussing. A user may scroll forwards and backwards in the video using the timeline 306. The timeline 306 may be disabled to ensure the entire media item has been broadcast, for example, when a user is required to complete the module as part of a training program.

Figure 4:
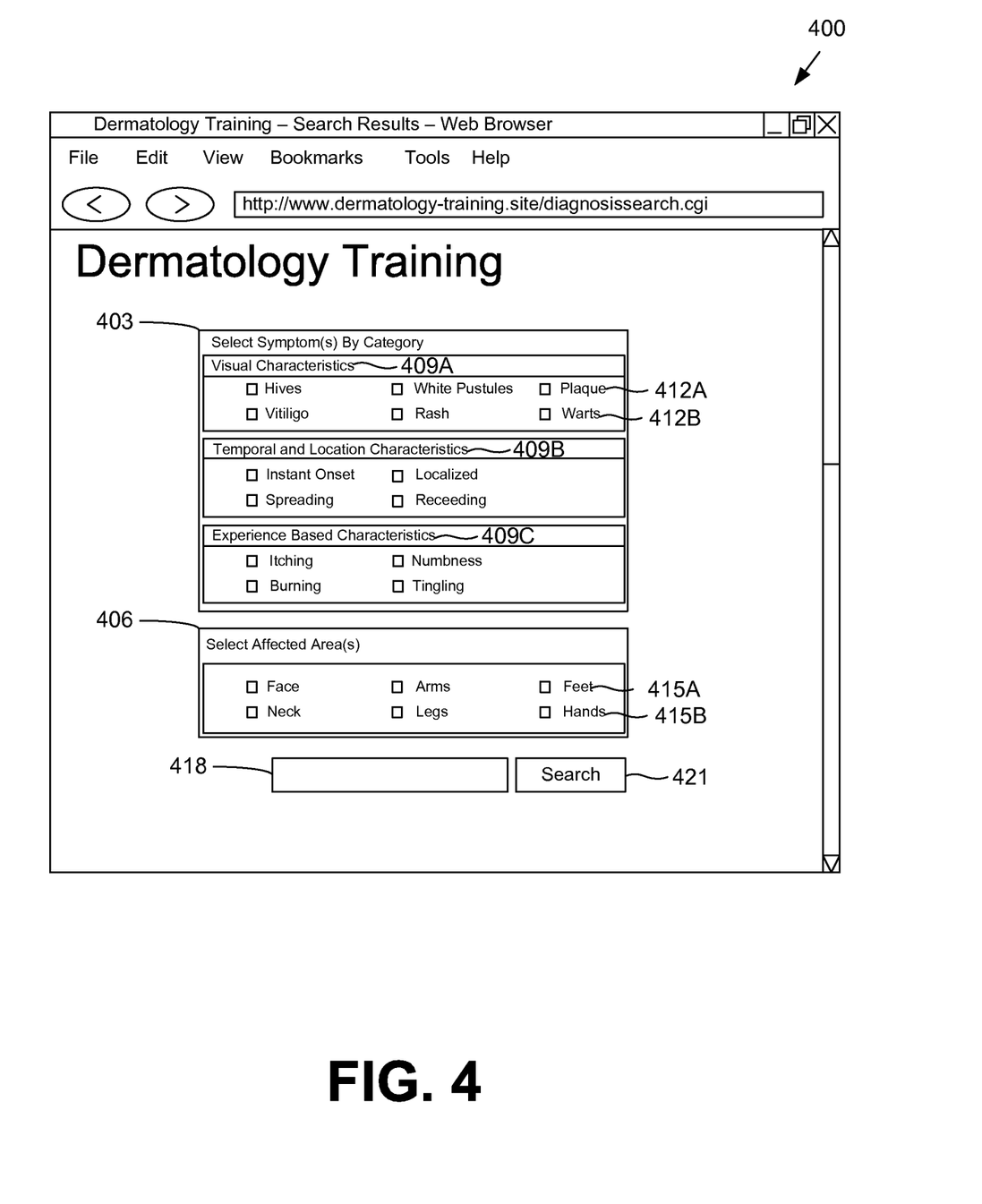
FIG. 4 illustrates a user interface rendered by a client in the networked environment of FIG. 1 according to various example embodiments.

With reference to FIG. 4, shown is an illustration of a search user interface 400 rendered on a display 169 (FIG. 1) of a client 106 (FIG. 1) in the networked environment of FIG. 1. A user may use the search user interface 400 to search for one or more potential diagnoses. In some embodiments, the search user interface 400 may be used to search for one or more modules. The search user interface 400 may include one or more symptoms 403, one or more characteristics/categories 409A-C, one or more affected areas 406, a search box 418, and a search button 421. The search user interface 400 may include one or more indicators for symptoms, categories, and/or affected areas, such as indicators 412A, 412B, 415A, and 415B. The search user interface 400 may be generated by the training application 118 (FIG. 1), for example, when a user selects the search for diagnosis button 224 (FIG. 2).

Figure 5:
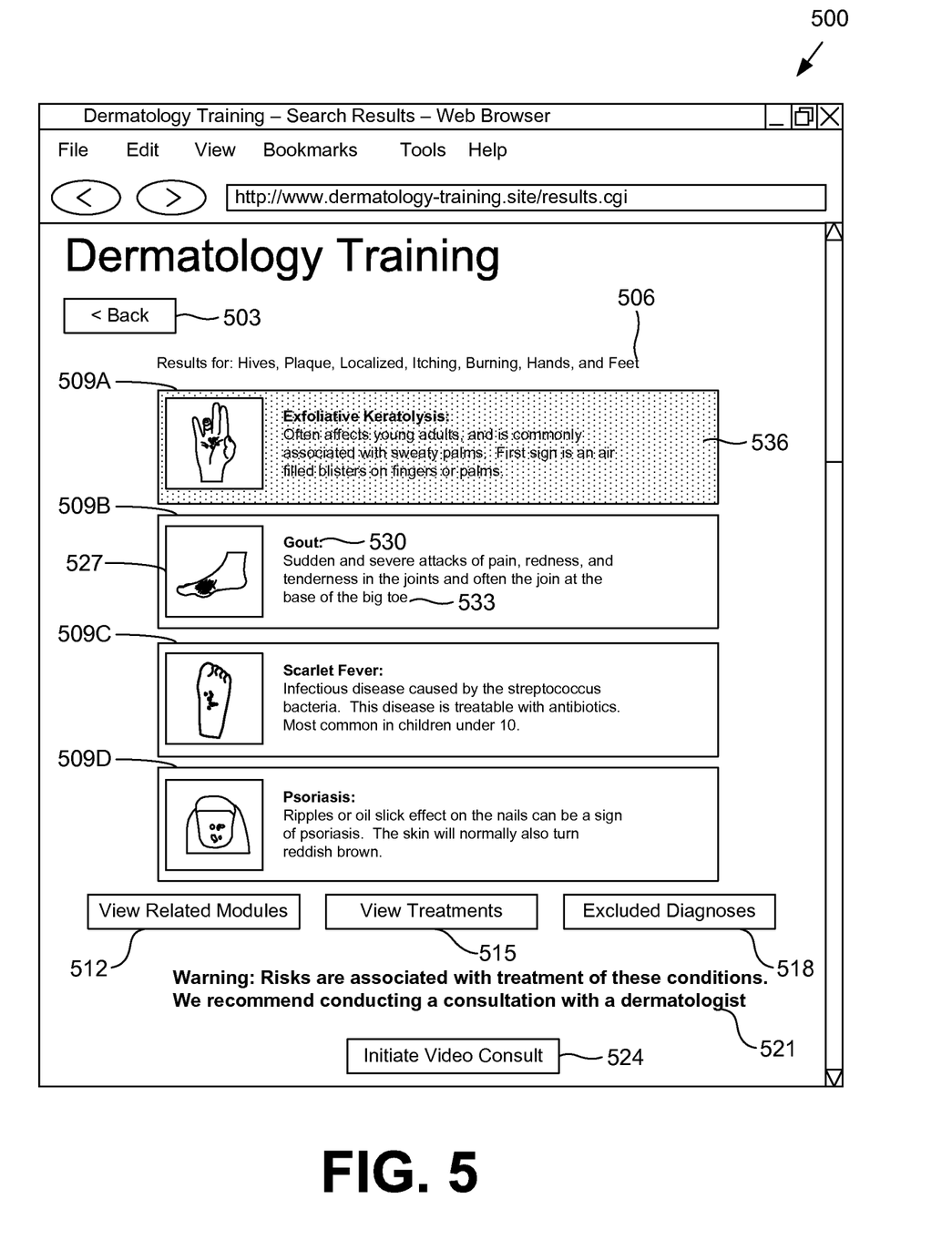
FIG. 5 illustrates a user interface rendered by a client in the networked environment of FIG. 1 according to various example embodiments.

With reference to FIG. 5, shown is an illustration of a search results user interface 500 rendered on a display 169 (FIG. 1) of a client 106 (FIG. 1) in the networked environment of FIG. 1. The search results user interface 500 may include a back button 503, description of the selected search criteria 506, one or more search results 509a-d, a view related modules button 512, view treatment button 515, an excluded diagnoses button 518, a warning message 521, and a initiate video consult button 524. The back button 503 may return the user to a previous screen. The selected search criteria 506 may include any basis upon which the training application 118 used to generate the search results, for example, symptoms, categories or characteristics, affected areas, search terms, and other basis. The search results 509a-d may include one or more pictures 527 depicting a symptom of the diagnosis on an individual, a title 530, and a description 533. In some embodiments, selecting a result from the search may highlight or gray the background of the selected search result, such as highlighting and/or graying 536. The search results user interface 500 may show module results meeting search requirements and/or potential diagnoses results.

The view related modules button 512 may show training modules that correspond to the search results, either individual results or as a group of results. The view treatments button 515 may advance to the user to diagnosis user interface 600 (FIG. 6) for the selected one of the search results. The excluded diagnoses button 518 may display information about diagnoses that the training application 118 excluded from the results. The information may also include a reason why each result was not included in the results. For example, the information may indicate that head lice were excluded because head lice does not include a symptom of burning and does not affect the hands and feet. The warning message 521 and/or initiate video consult button 524 may be conditionally included when risks associated with a treatment of one of the diagnoses and/or a risk of mistreatment of one of the diagnoses exceeds a threshold risk. In some embodiments, the threshold is customized for a specific user using one or more of the credentials of the user or user data of the user, such as credentials 151 and user data 148 (FIG. 1).

Figure 6:
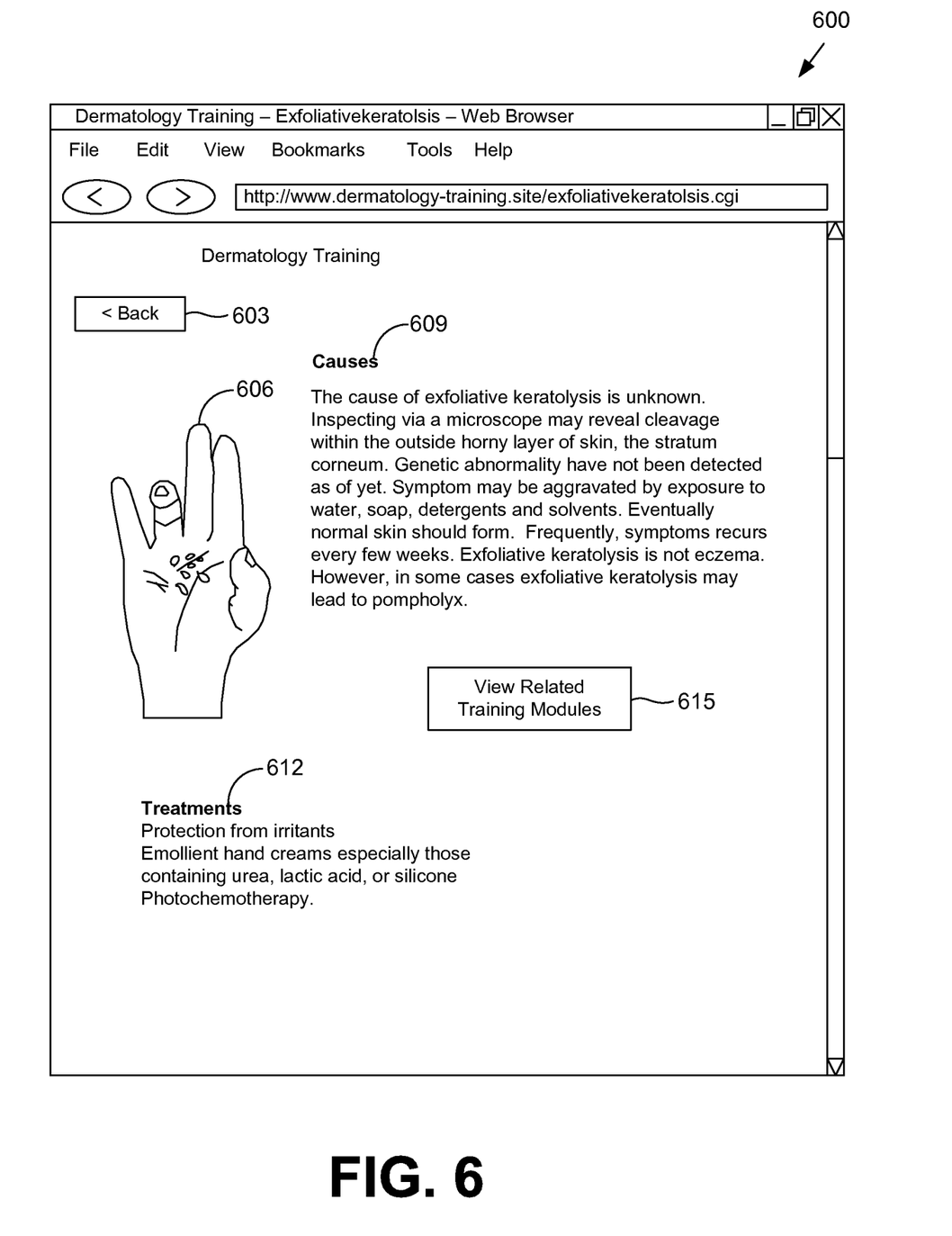
FIG. 6 illustrates a user interface rendered by a client in the networked environment of FIG. 1 according to various example embodiments.

With reference to FIG. 6, shown is an illustration of a diagnosis user interface 600 rendered on a display 169 (FIG. 1) of a client 106 (FIG. 1) in the networked environment of FIG. 1. The diagnosis user interface 600 may include a back button 603, one or more pictures 606 depicting one or more symptoms of the diagnosis on an individual, cause details 609, treatment details 612, and view related modules button 615. The back button 603 may return the user to a previous screen. The one or more pictures 606, the cause details 609, and treatments 612 may individually be stored in diagnoses data 124 (FIG. 1) and/or received from a third party source, such as an image search on one or more search engines. The view related modules button 615 may show training modules that correspond to the search results, either individual results or as a group of results.

Figure 7:
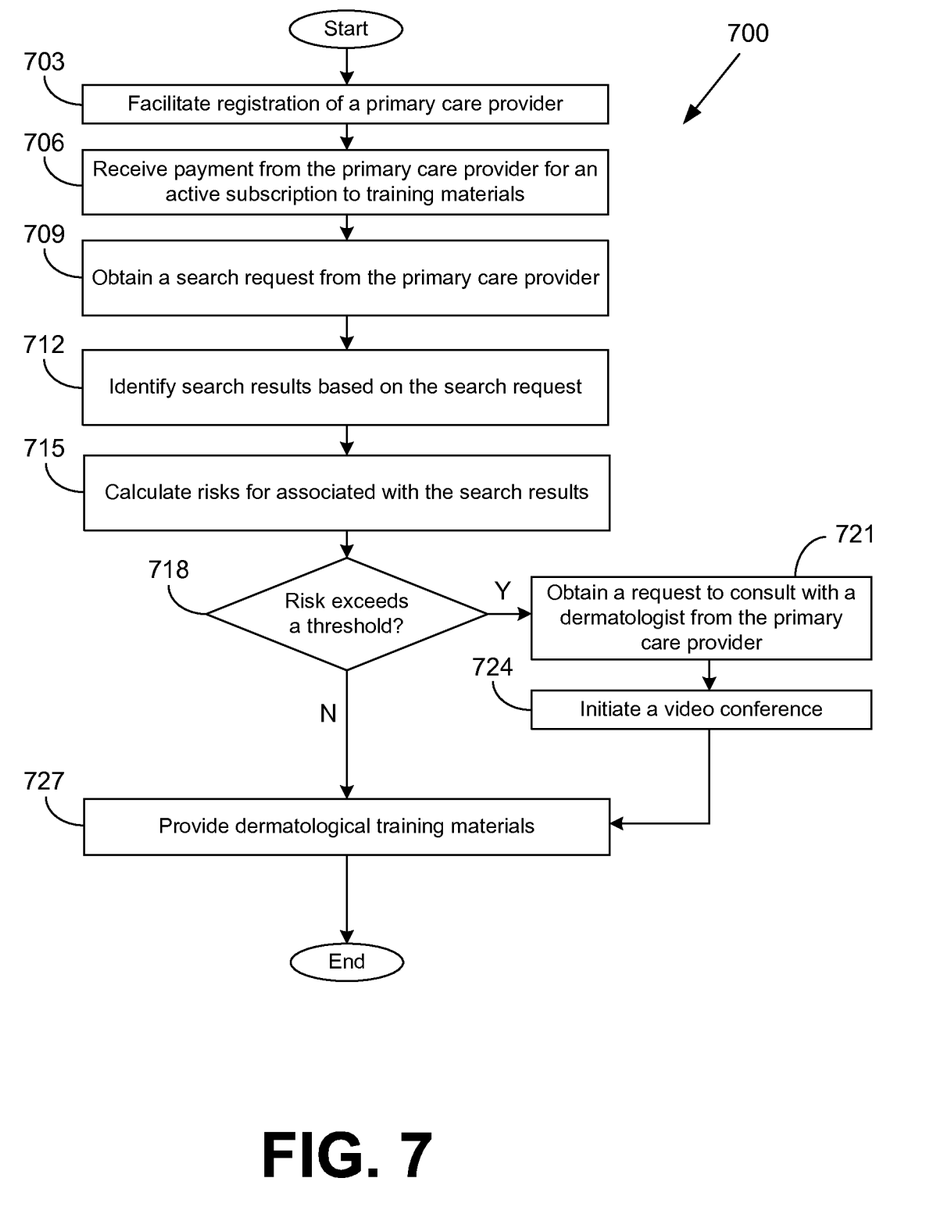
FIG. 7 illustrates an example flowchart of certain functionality implemented by portions of a training application executed in a computing environment in the networked environment of FIG. 1 according to various embodiments of the present disclosure.

Referring next to FIG. 7, shown is training process 700 illustrated as a flowchart that provides one example of the operation of a portion of the training application 118 according to various embodiments. It is understood that the flowchart of FIG. 7 provides merely an example of the many different types of functional arrangements that may be employed to implement the operation of the portion of the training application 118 as described herein. As an alternative, the flowchart of FIG. 7 may be viewed as depicting an example method implemented in the computing environment 103 (FIG. 1) according to one or more embodiments.

Beginning with box 703, the training application 118 involves facilitating the registration of a user, such as a primary care provider. For example, a user may create an account on the system by filling out information on a registration form. The training application 118 may store the information of the user in data store 112 (FIG. 1), for example, in users 127 (FIG. 1). The training application 118 may require an administrator to approve the user prior to providing access to content. The user may be required to submit formal documents to an administrator before the administrator approved any medical credentials in the computing environment.

At box 706, the training application 118 involves receiving a payment from the user for an active subscription to one or more dermatology training materials. For example, training application 118 may receive a payment via network 109. The user may subscribe to all of the modules using an ongoing subscription, purchase access to all modules for a fixed period of time, or purchase access to one or more modules on an individual basis. The training application 118 may obtain payment for video consultations with dermatologists and/or a subscription for video consultations. The training application 118 may facilitate the renewal of a subscription including receiving payment for the renewal. The training application 118 may offer a discount compared to the initial subscription price for a user that renews their subscription. The training application 118 may also offer a discounted initial trial period and an increased price from the trial period when the subscription renews.

At box 709, the training application 118 involves obtaining a search request from a user. The search request may include one or more criteria to search for, such as one or more affected areas and one or more symptoms including visual characteristics, temporal characteristics, locational characteristics, experience based characteristics, and other aspects of the dermatology condition. The search request may be a search request for a training module and/or a search request to diagnose a condition. The search request may be facilitated by a user interface, such as search user interface 400 (FIG. 4).

At box 712, the training application 118 involves identifying search results for the search request. The training application 118 may perform various queries to the one or more data bases 112 (FIG. 1), such as querying the training modules 121 (FIG. 1) and/or diagnoses data 124 (FIG. 1). The training application 118 may identify all diagnoses in diagnoses data 124 that fit all of the requirements provided by the user. As a non-limiting example, a user may supply that a patient has hives, plaque, itching, and burning on his or her hands and feet and that the symptoms are localized/not spreading. In this example, the training application 118 may identify the search results as the entries for exfoliative keratolysis, gout, scarlet fever, and psoriasis in the diagnoses data 124 with each of these symptoms in symptoms 145 associated with the diagnoses.

At box 715, the training application 118 involves calculating risks associated with the search results. The training application 118 may calculate risks associated with treating a patient having a condition described in one or more of the search results. The training application 118 may calculate the risk of treating each of the conditions by using risk 142 or data from external server 107. For example, the training application 118 may determine that the medicine associated with chemotherapy for cancer exceeds a risk threshold, and alert a user of the risks associated with the potential diagnosis. The training application 118 may also determine that treatment associated with one condition in the search results could cause damage if a patient had a different condition in the search results. For example, the training module may warn a user return search results of skin cancer and an immune system disease, where chemotherapy may cause an undesirable effect on the immune system.

At box 718, the training application 118 involves determining if the risk meets a threshold risk. The training application 118 may determine the threshold risk based at least in part on data in users 127 (FIG. 1) such as based at least in part on a credentials of the user or previously input from the user. If the threshold risk is met, the training application 118 may proceed to box 721, otherwise the training application 118 may proceed to box 727. At box 721, the training application 118 involves obtaining a request to consult with a dermatologist from the user. For example, the training application 188 may obtain a request from a primary care provider to video conference with a dermatologist when risk to a patient may exceed a specified level. The request may include a one or more criteria for one or more dermatologists that the user wishes to consult/conference with. At box 724, the training application 118 involves initiating a video conference with the user and one or more dermatologists meeting the criteria from the user request. The training application 118 may send a request to a client 106 associated with each of the one or more dermatologists to enter into a video chat via a camera connected to or part of the client 106. Upon obtaining an indication of an answer from one or more participants, the training application 118 may connect each answered participant via a video conference.

At box 727, the training application 118 involves providing dermatological training materials to the client 106. The dermatological training materials may comprise one or more training modules, for example, training user interface 300. The dermatological training materials may comprise diagnostic information such as diagnosis user interface 600 (FIG. 6). The training application 118 may ensure that a maximum number of clients 106 (FIG. 1) corresponding to a user are not currently accessing the computing environment 103, and if the maximum number of clients is exceeded, restrict access to the dermatological training materials. The training application 118 may ensure that the user has a valid and active subscription for the dermatological training materials before providing the dermatological training materials to the user. Otherwise, the training application 118 may restrict the user from accessing the dermatological training materials.

Figure 8:
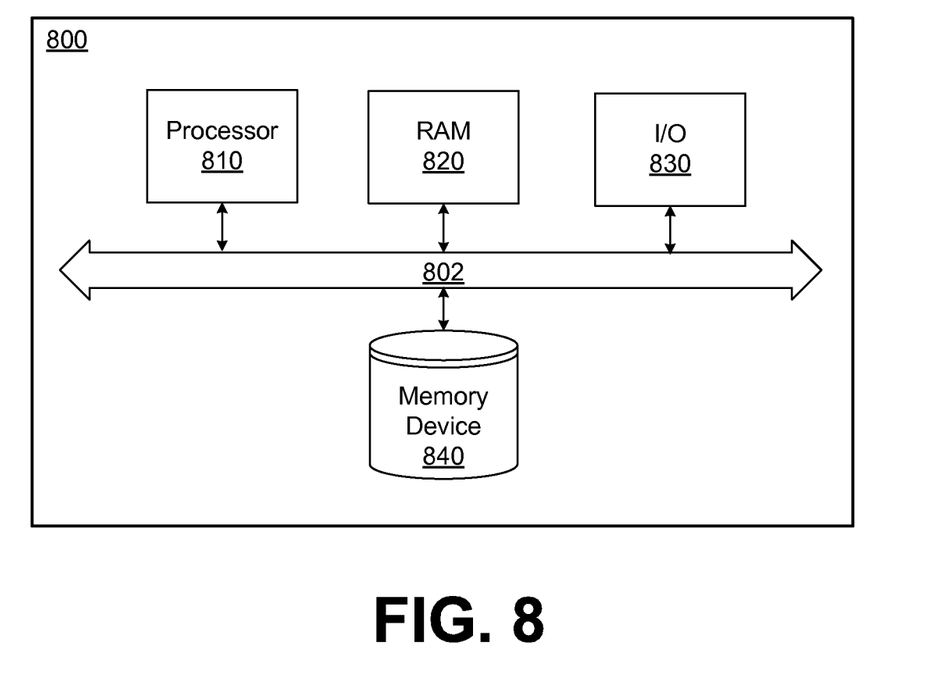
FIG. 8 is a schematic block diagram that illustrates an example computing environment and client(s) employed in the networked environment of FIG. 1 according to various embodiments.

With reference to FIG. 8, shown is a schematic block diagram of the computing environment 103, client 106, and/or external server 107 according to an embodiment of the present disclosure. The computing environment 103, client(s) 106, and external server 107 include one or more computing devices. Each computing device includes at least one processor circuit, for example, having a processor 810 and a memory 840, both of which are coupled to a local interface 802. To this end, each computing device may comprise, for example, at least one server computer or like device. The local interface 802 may comprise, for example, a data bus with an accompanying address/control bus or other bus structure as can be appreciated.

Stored in the memory 840 are both data and several components that are executable by the processor 810. In particular, stored in the memory 840 and executable by the processor 810 are training application 118 and client application 166, and potentially other applications. Also stored in the memory 840 may be a data store 112 and other data. In addition, an operating system may be stored in the memory 840 and executable by the processor 810.

It is understood that there may be other applications that are stored in the memory 840 and are executable by the processor 810 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, or other programming languages.

A number of software components are stored in the memory 840 and are executable by the processor 810. In this respect, the term "executable" means a program file that is in a form that can ultimately be run by the processor 810. Examples of executable programs may be, for example, a compiled program that can be translated into machine code in a format that can be loaded into a random access portion of the memory 840 and run by the processor 810, source code that may be expressed in proper format such as object code that is capable of being loaded into a random access portion of the memory 840 and executed by the processor 810, or source code that may be interpreted by another executable program to generate instructions in a random access portion of the memory 840 to be executed by the processor 810, etc. An executable program may be stored in any portion or component of the memory 840 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 840 is defined herein as including both volatile and nonvolatile memory and data storage components. Volatile components are those that do not retain data values upon loss of power. Nonvolatile components are those that retain data upon a loss of power. Thus, the memory 840 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 810 may represent multiple processors 810 and/or multiple processor cores and the memory 840 may represent multiple memories 840 that operate in parallel processing circuits, respectively. In such a case, the local interface 802 may be an appropriate network that facilitates communication between any two of the multiple processors 810, between any processor 810 and any of the memories 840, or between any two of the memories 840, etc. The local interface 802 may comprise additional systems designed to coordinate this communication, including, for example, performing load balancing. The processor 810 may be of electrical or of some other available construction.

Although training application 118 and client application 166, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

The flowchart of FIG. 7 shows the functionality and operation of an implementation of portions of the training application 118. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 810 in a computer system or other system. The machine code may be converted from the source code, etc. If embodied in hardware, each block may represent a circuit or a number of interconnected circuits to implement the specified logical function(s).

Although the flowchart of FIG. 7 shows a specific order of execution, it is understood that the order of execution may differ from that which is depicted. For example, the order of execution of two or more blocks may be scrambled relative to the order shown. Also, two or more blocks shown in succession in FIG. 7 may be executed concurrently or with partial concurrence. Further, in some embodiments, one or more of the blocks shown in FIG. 7 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including training application 118 and client application 166, that comprises software or code can be embodied in any non-transitory computer-readable medium for use by or in connection with an instruction execution system such as, for example, a processor 810 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, including training application 118 and client application 166, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device, or in multiple computing devices in the same computing environment 103. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A non-transitory computer-readable medium embodying a program that, when executed by at least one computing device being configured to at least:
   implement dermatology training materials, wherein the dermatology training materials are divided into a plurality of modules, each of the modules directed toward training primary care providers in diagnosing and treating a specific skin condition;
   restrict access to the dermatology training materials based at least in part on whether a user has an active subscription;
   search the plurality of modules based at least in part on at least one criteria obtained from the user regarding information describing a problem of a patient including an undiagnosed symptom and an affected area;
   identify a plurality of potential diagnoses from a plurality of dermatological diagnoses based at least in part on the information describing the problem of the patient and information describing the plurality of dermatological diagnoses;

cause rendering of a user interface comprising a plurality of search results from the plurality of modules that meet the at least one criteria, information regarding a subset of the plurality of modules excluded from the plurality of search results, and information regarding a subset of the plurality of dermatological diagnoses excluded from a plurality of potential diagnoses;

calculate a risk associated with a treatment corresponding to each of the plurality of potential diagnoses, wherein calculating the risk comprises calculating the risk of treating each of the plurality of potential diagnoses;

in response to determining the risk exceeds a threshold, include the risk associated with the treatment in the user interface and provide an option to consult via video conference with at least one dermatologist;

the threshold for the primary care provider user based at least in part on one or more credentials of the primary care provider user; and in response to determining the risk exceeds the threshold, and further in response to obtaining a consultation request associated with the option, the consultation request including at least one selection criteria for selecting the at least one dermatologist, cause a client associated with the user to stream video and audio.

2. The non-transitory computer-readable medium of claim 1, wherein the at least one computing device is further configured to at least:

obtain an image or a video illustrating a symptom;

process the image or the video using pattern recognition to generate a plurality of characteristics of the symptom; and generating the at least one criteria based in part on the plurality of characteristics.

3. The non-transitory computer-readable medium of claim 1, wherein the program further causes the at least one computing device to restrict access based at least in part on whether the user is a primary care provider, the primary care provider being at least one of: a primary care physician practicing family medicine, pediatrics, obstetrics/gynecology, surgery, or emergency room medicine, a nurse practitioner, or a physician assistant.

4. A system, comprising:

a data store; and at least one computing device in communication with the data store, the at least one computing device being configured to at least:

facilitate registration by a primary care provider user;

receive payment from the primary care provider user for an active subscription to dermatology training materials;

obtain a search request from a client associated with the primary care provider user including information describing a problem of a patient including an affected area;

provide dermatology information to the client via a network when the primary care provider user has the active subscription;

identify a plurality of potential diagnoses from a plurality of dermatological diagnoses based at least in part on the information describing the problem of the patient and information describing the plurality of dermatological diagnoses, the dermatology information comprising information regarding a subset of the plurality of dermatological diagnoses excluded from a plurality of potential diagnoses;

calculate a risk associated with a treatment corresponding to each of the plurality of potential diagnoses, wherein the dermatology information comprises the risk associated with the treatment and the plurality of potential diagnoses, wherein calculating the risk comprises calculating the risk of treating each of the plurality of potential diagnoses;

in response to determining the risk exceeds a threshold, include the risk associated with the treatment in the dermatology information and provide an option to consult via video conference with at least one dermatologist; and in response to determining the risk exceeds the threshold, and further in response to obtaining a consultation request associated with the option, the consultation request including at least one selection criteria for selecting the at least one dermatologist, cause a client associated with the primary care provider user to stream video and audio.

5. The system of claim 4, wherein the at least one computing device is further configured to at least:

determine, for each of the plurality of potential diagnoses, a likelihood that the treatment corresponding to one of the plurality of potential diagnoses could negatively impact someone having a condition corresponding to another one of the plurality of potential diagnoses; and in response to determining that the treatment corresponding to the one of the plurality of potential diagnoses could negatively impact someone having the condition, include the likelihood that the treatment could negatively impact the patient in the dermatology information.

6. The system of claim 4, wherein the dermatology information further comprises a reason why individual ones of the subset of the plurality of dermatological diagnoses were excluded.

7. The system of claim 4, wherein the information describing the problem of the patient further includes at least one symptom, and at least one category of the problem; and the dermatology training materials comprise a plurality of separate modules, wherein at least one of the separate modules are eligible for individual subscription.

8. The system of claim 4, wherein the dermatology training materials comprise a plurality of separate modules, at least one of the separate modules are eligible for individual subscription, and the separate modules include an acne module, an office procedures module, an eczema module, and an atopic dermatitis module.

9. The system of claim 4, wherein the at least one computing device is further configured to receive payment from the primary care provider user for a renewal subscription to the dermatology training materials.

10. The system of claim 4, wherein the dermatology training materials include at least one of a presentation directed at specific skin conditions, a video of a dermatology office procedure, or an audio narration.

11. The system of claim 4, wherein the dermatology training materials include one or more images of patients exhibiting a skin condition.

12. A method for delivering dermatology-specific training to primary care providers, the method comprising:

registering, via at least one computing device, a primary care provider user;

obtaining, via the at least one computing device, a request from a client associated with the primary care provider user to search dermatology training materials, the request to search dermatology training materials including information describing a problem of a patient including an affected area;

identifying, via the at least one computing device, a plurality of potential diagnoses from a plurality of dermatological diagnoses based at least in part on the information describing the problem of the patient and dermatology information describing the plurality of dermatological diagnoses, the dermatology information comprising information regarding a subset of the plurality of dermatological diagnoses excluded from a plurality of potential diagnoses;

providing, via the at least one computing device, the dermatology training materials to the client when the primary care provider user is determined to be valid, the dermatology training materials comprising information regarding a subset of a plurality of dermatological diagnoses excluded from the plurality of potential diagnoses;

calculating a risk associated with a treatment corresponding to each of the plurality of potential diagnoses, wherein the dermatology information comprises the risk associated with the treatment and the plurality of potential diagnoses, wherein calculating the risk comprises calculating the risk of treating each of the plurality of potential diagnoses;

in response to determining the risk exceeds a threshold, including the risk associated with the treatment in the dermatology information and providing an option to consult via video conference with at least one dermatologist; and in response to determining the risk exceeds the threshold, and further in response to obtaining, via the at least one computing device, a consultation request associated with the option, the consultation request including at least one selection criteria for selecting the at least one dermatologist, causing, via the at least one computing device, a client associated with the primary care provider user to stream video and audio.

13. The method of claim 12, further comprising:
selecting, via the at least one computing device, the at least one dermatologist that meets the at least one selection criteria from a plurality of dermatologists, where each of the plurality of dermatologists has indicated availability for a consult.

14. The method of claim 13, further comprising:
obtaining, via the at least one computing device, a request from the primary care provider user to terminate the video conference; and
calculating, via the at least one computing device, a cost to charge the primary care provider user for the video conference based in part on a time of the video conference and the at least one criteria.

15. The method of claim 13, further comprising:
obtaining, via the at least one computing device, medical records of the patient associated with the primary care provider user; and
generating, via the at least one computing device, an overlay on a user interface of the video conference for each of the at least one dermatologist including the medical records of the patient.

16. The method of claim 15, further comprising:
obtaining, via the at least one computing device, identifying information for the patient, wherein the medical records are obtained via an electronic medical record system using the identifying information for the patient.

17. The method of claim 12, wherein the dermatology training materials include a plurality of modules, each of the modules directed at treating a specific skin condition.

18. The method of claim 12, further comprising determining, via the at least one computing device, whether the client corresponds to one of a maximum number of clients corresponding to the primary care provider user that are permitted to access the dermatology training materials.

19. The method of claim 12, further comprising determining, via the at least one computing device, that the primary care provider user is valid when the primary care provider user has an active subscription; and facilitating, via the at least one computing device, a renewal of the active subscription for a discounted price relative to an initial subscription price.

20. The method of claim 12, further comprising:
customizing, via the at least one computing device, the threshold for the primary care provider user based at least in part on one or more credentials of the primary care provider user.

* * * * *